(12) United States Patent
Engelman

(10) Patent No.: US 7,429,254 B1
(45) Date of Patent: Sep. 30, 2008

(54) ARTICULATED ANKLE FOOT BRACE HAVING A MALLEOLAR WINDOW

(76) Inventor: Ian Engelman, 3 Rhonda Dr., Scarborough, ME (US) 04106

( * ) Notice: Subject to any disclaimer, the term of this patent is extended or adjusted under 35 U.S.C. 154(b) by 174 days.

(21) Appl. No.: 11/380,970

(22) Filed: May 1, 2006

(51) Int. Cl.
*A61F 13/00* (2006.01)
(52) U.S. Cl. .............................. 602/27; 602/16; 602/23
(58) Field of Classification Search .................. 602/5, 602/16, 27–29, 65, 23; 128/882; 36/140, 36/132
See application file for complete search history.

(56) References Cited

U.S. PATENT DOCUMENTS

| | | | | |
|---|---|---|---|---|
| 1,205,206 A | * | 11/1916 | Hofmeister | 36/89 |
| 5,027,801 A | * | 7/1991 | Grim | 602/16 |
| 5,056,509 A | * | 10/1991 | Swearington | 602/29 |
| 5,226,875 A | * | 7/1993 | Johnson | 602/27 |
| 5,759,168 A | * | 6/1998 | Bussell et al. | 602/27 |
| 5,778,563 A | * | 7/1998 | Ahlbaumer | 36/88 |
| 2002/0029009 A1 | * | 3/2002 | Bowman | 602/27 |
| 2006/0084899 A1 | * | 4/2006 | Verkade et al. | 602/27 |

OTHER PUBLICATIONS

Dr. Michelle M. Lusardi and Dr. Caroline C. Nielsen "Orthotics and Prosthetics in Rehabilitation", Copyright Saunders Elsevier St. Louis, Missury 2007, ISBN 13-978-0-7506-7479-9. p. 222.
Dr. Ron Seymour, Prosthetics and orthosis: lower limbs and spinal, Copyright by Lippinkot Williams & Wilkins, Philadelphia, Pennsylvania, 2002, ISBN 0-7817-2854-1, pp. 78-79.

* cited by examiner

*Primary Examiner*—Kim M Lewis

(57) ABSTRACT

An ankle foot brace having a heel stirrup, a lower lateral and medial uprights, and an upper lateral and medial uprights hinged to the respective lower uprights. A malleolar window, preferably with a membrane extending thereupon, creates a hammock like support for the malleolus. The hinge point on the side having the malleolar window is moved upwards and preferably back from the apex of the malleolus. Doing so allows the application of tolerable corrective forces at this location to help prevent undesired movement of the malleolus. If a membrane is not employed, the window allows application of corrective forces in the vicinity of the malleolus without causing pain thereto.

10 Claims, 4 Drawing Sheets

ARTICULATED ANKLE FOOT BRACE HAVING A MALLEOLAR WINDOW

FIELD OF THE INVENTION

This invention relates generally to a brace, and more particularly to an ankle foot brace having a malleolar window.

BACKGROUND OF THE INVENTION

To assist in understanding the present invention and its various aspects, these specifications and their attached claims will refer to certain geometrical terms such as up, down, horizontal and vertical, forward and backward. The reference point to such geometrical directions should be taken to be a human foot. Thus for example, the term forward should be construed as extending from the heel substantially in the general direction of the toes, and backward refers generally to the opposite direction. Similarly the term horizontal should be construed as the general plane on which normal foot at rest, and planes parallel thereto, with the heel defining a reference plane commonly referred to as bottom. Similarly the term vertical extends at or about 90 degrees to the horizontal plane, and upward or downward to directions extending from the reference plane, with upwards implying the direction towards the knee. However as human legs and feet do not follow clear geometrical shapes the terms also extend to angles different from 90 degrees and to surfaces diverting form the flat plane, or generally to that which the person skilled in the art will recognize as the customary and ordinary meaning as relating to the human anatomy of the foot, with the heel being a reference point.

Ankle foot instabilities can be generally categorized in two ways: Medial Instability and Lateral Instability.

The term "medial instability" has been described several different ways within different professions and in different areas of the country. Orthotists commonly refer to this combination of anatomical conditions as "IRD"; internal rotary deformity. This condition describes the internal rotation of the tibia in relation to the foot. The term Internal should be construed to mean as viewed downward on the cross-section of the tibia, the forward edge moves medially. Most often the clinical findings for this are: forefoot abduction, hindfoot valgus, collapsed or partially collapsed medial longitudinal arch. Other professions have referred to this condition as flat foot, pes plantus, eversion and excessive pronation. The orthotic treatment for Medial instability is challenging. As the body weight exerts strong forces which need to be controlled, the condition is often only partially correctable.

Similarly, definitions and names abound for the term "Lateral Instability". The common description is "twisting of the ankle". The foot is inverted excessively to the point at which the weight line falls to the lateral side of the mid-tarsal joint and the hindfoot and forefoot are to the medial side of the tibia. Orthotists commonly refer to this condition as External Rotational Deformity (ERD). This condition is sometimes characterized by a verrous hindfoot, an adducted forefoot and a supinated midfoot. Pes cavous or excessive supination or excessive inversion are other common names for lateral instability.

Common treatment for Lateral instability dictates inter alia the use of a brace. Common brace designs may be seen in the sports industry. These can be made of soft flexible material or of rigid plastic. Such braces provide some protection to the user by reducing the extent of injury from twisting of the ankle.

Some existing solutions provide support for the foot and ankle, but lack an articulation, therefore restricting the plantarflexion/dorsiflexion movement of the ankle. Other articulated designs commonly have tolerance issues with pressure on the lateral malleolus or don't recruit the benefits of stability one can get from controlling this part of the foot and ankle.

Common treatment for Medial instability dictates inter alia the use of a brace or orthotic foot inlay. Common brace designs have been provided by Orthotists and Podiatrists. These designs are generally custom designs. Mostly, they are constructed to have an articulation at or near the medial and lateral malleolus. This misunderstood need to locate the articulation near the malleoli has resulted in the forfeit of a strategic and effective area of control. During the stance phase, there is significant medial movement of the medial malleoli. Restricting this movement provides an opportunity for improved motion control. Old metal and leather style braces would incorporate a leather "T" strap which would be wrapped around the lateral upright and around the medial malleolus. Nowadays plastic is generally used for brace designs.

Furthermore, an orthosis takes a lot of room in the shoe and often the user of orthopedic braces faces difficulty finding shoes that are big enough to accommodate the brace and foot combination.

Within the field of podiatry, the medial instability problem is described as posterior tibialis dysfunction (PTD). The theory describes the failure of the posterior tibialis muscle and tendon to uphold the medial side of the foot. The result is a medial collapse of the midfoot, plantarflexion of the talus, and navicular and first cuniform movement downwards. Most often this is in combination to a plantarflexion contracture and external bracing solutions are partial solutions. However, orthotic inlays and braces can help reduce the amount of medial collapse and therefore significantly reduce the pain associated with the Medial instability.

The portion of the foot that goes through the most excursion during weight bearing for a Medial Instability patient, is the medial malleolus. Effective control of the movement of the medial malleolus is therefore highly desirable. However, most brace designs to date avoid movement control of the medial malleolus, because of general lack of supporting soft tissue over this bony prominence. The lack of soft tissue makes the medial malleolus intolerant of high corrective pressures. Yet, if controlled, the medial malleolus likely provides the most effective location in the management of Medial Instability.

Therefore, there is a clear and heretofore unanswered need for brace design that will reduce the shoe size, while providing good support and motion control, preferably with controlling the medial or lateral malleolus as needed. The present invention is aimed at providing such a brace.

SUMMARY OF THE INVENTION

It is an object of the present invention to resolve the shortcomings described above. In addition to the other various aspects of the invention, it uses many available areas for corrective applied force. Having more support area reduces the tendency to have localized pressure by spreading the pressure out over a greater area.

The most preferred embodiment of the invention moves the medial joint upwards and back from the apex of the medial malleolus. Doing so allows the application of tolerable corrective forces at this location to help prevent medial movement of the malleolus. The application of the force is achieved by creating a window near the malleolus, and by creating a hammock a relatively flexible material.

Therefore, in its most basic form, the present invention provides an ankle brace to be worn by a wearer to help prevent eversion or inversion of the foot and ankle. The brace having a heel stirrup 25, a horizontally and forwardly extending footplate 22, and medial lower upright 17 and lateral lower upright 7 portions extending vertically from the stirrup. A medial upper upright 5 and a lateral upper upright 15 are pivotally coupled to corresponding medial and lateral lower uprights at medial pivot point (13) and lateral pivot point (23), respectively. In one embodiment of the invention directed primarily to treating the medial instability, the medial lower upright defines an aperture 10, through which the medial malleolus may protrude. Similarly, in another preferred embodiment, the lateral lower upright define an aperture 101 for allowing the lateral malleolus to protrude. Either aperture may be equipped with a flexible membrane fully or partially across the aperture to provide extended support and cushioning to the medial and/or lateral malleolus. The invention applies equally to both lateral and/or medial instabilities, and an embodiment is selected to best address the corresponding problem.

Different aspects of the invention use a unique system and approach which provides correction more effectively and more comfortably than existing solutions. The invention maximizes the use of available areas for applying corrective forces, and thus reduces the tendency to have localized pressure by spreading the pressure out over a greater area.

Therefore in an aspect of the present invention there is provided a hinged ankle foot brace comprising a heel stirrup having a horizontal footplate. A medial and a lateral lower uprights extend substantially vertically from the stirrup, one of the lower uprights defining an aperture dimensioned for receiving at least a portion of a malleolus disposed therein. A medial and a lateral upper uprights are coupled to their respective lower uprights. The lateral upper upright is hinged to the lower lateral upright, and the medial upper upright hinged to the medial lower upright, wherein the respective upper upright coupled to the respective lower upright having the aperture, is hinged upwardly to the center of the aperture, and the second upper upright is coupled to the respective lower upright proximal to the malleolus opposite the malleolus at least partially disposed within said aperture.

Therefore, in one embodiment of the invention direct to treating patients with medial instability, the upright having the aperture is the medial lower upright, and the medial upper upright is hinged to the lower medial upright upwardly and preferably posteriorly to the center of the aperture, and the lateral upper upright is hinged to the lateral lower upright adjacent to the lateral malleolus. The term 'center of the aperture' should be construed to mean the approximate center a medial malleolus of a patient wearing the brace, while the term adjacent to the lateral malleolus should be construed to mean closer to the center of the lateral malleolus of same patient, and preferably at the or about the center thereof.

Similar to the embodiment but directed at treating patients with lateral instability, the upright having the aperture is the lateral lower upright, the lateral upper upright is hinged to the lateral lower upright upwardly to the aperture, and the medial upper upright is hinged to said medial lower upright adjacent to the medial malleolus.

Optionally, the more preferred embodiment provide for a hinged ankle foot brace having either lateral or medial window, and further comprising a membrane extending over said aperture. Most preferably the membrane comprises a cushioning inner portion, and a resilient outer portion.

Further optionally there is provided a hinged ankle foot brace wherein the footplate has a longitudinal cutout such that when the brace is worn by a patient, the footplate extends laterally from the medial side of a foot, up to but not under the fifth metatarsal bone of the patient.

SHORT DESCRIPTION OF DRAWINGS

The summary above and the following detailed description will be better understood in view of the enclosed drawings which depict details of preferred embodiments. It should however be noted that the invention is not limited to the precise arrangement shown in the drawings and that the drawings are provided merely as examples.

DETAILED DESCRIPTION

Figure 1:
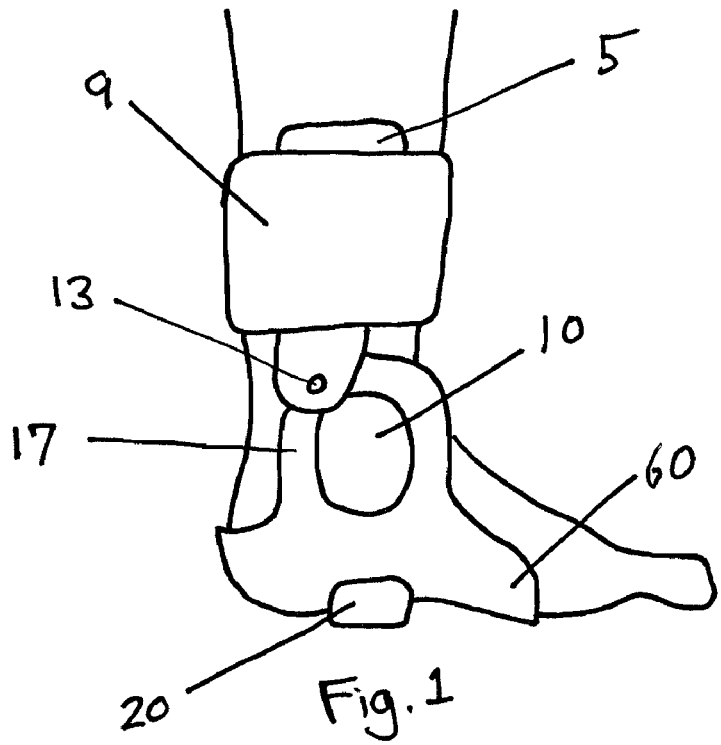
FIG. 1 shows the medial side of a preferred embodiment of the invention as applied to a foot and medial malleolus.
Figure 2:
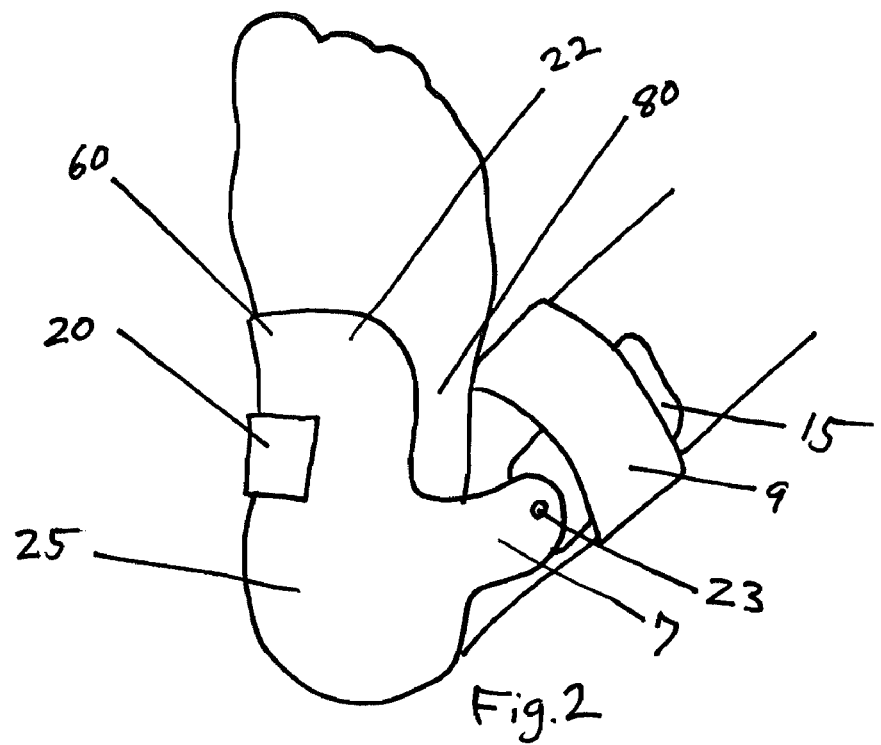
FIG. 2 shows the underside of the preferred embodiment of the invention on a foot and ankle.
Figure 3:
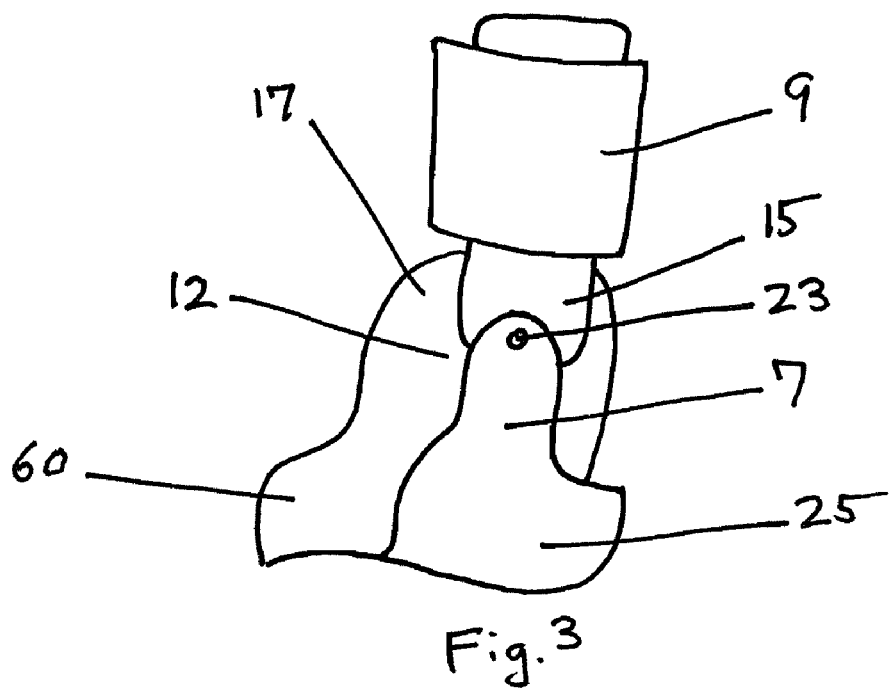
FIG. 3 shows the lateral side of a preferred embodiment of the invention as applied to a Medial Instability condition.
Figure 4:
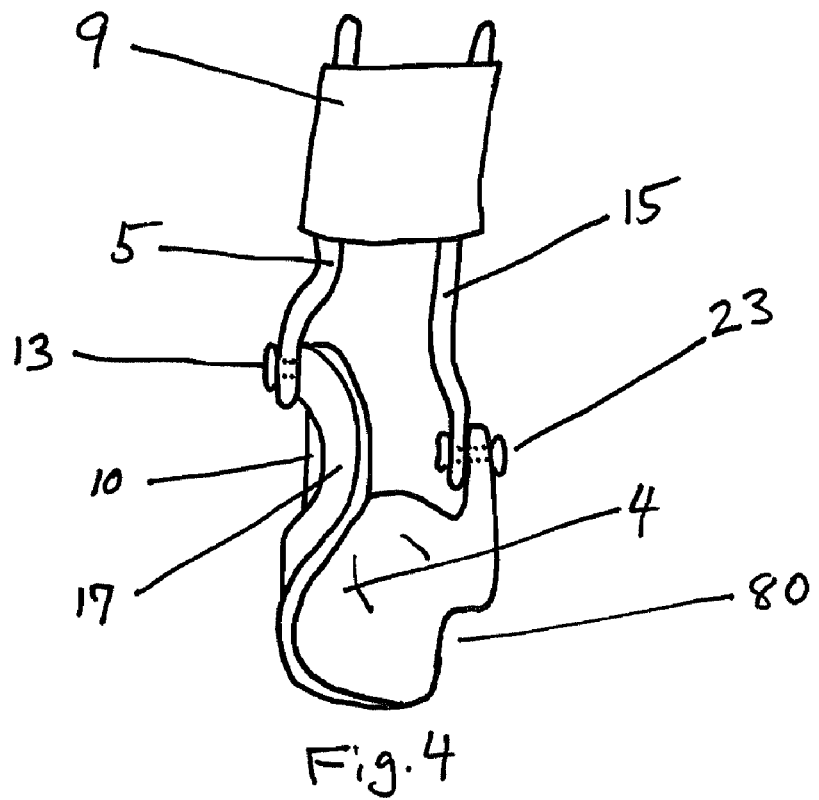
FIG. 4 shows the front view of the preferred embodiment of the invention as it applies to a Medial Instability condition.

The following embodiments will be described in details by way of guidance and example to assist the skilled person in implementing certain aspects of the invention.

As will be clear to the skilled in the art, an ankle brace requires a heel stirrup 25 with horizontal bottom section and upwardly extending lateral lower upright 7 and medial lower upright 17. Common brace designs further utilize upper medial 5 and upper lateral 15 uprights, hinged respectively to the lower medial and lateral uprights. The combination of the respective lower and the upper uprights may be considered, and are so termed herein, as a vertical wall of the brace.

For clarity, the following will describe a brace design directed to assisting patients suffering from medial instability. The skilled in the art will recognize that for treating lateral instability the description made herein needs to reversed, i.e. the description of the medial uprights should be replaced by the lateral uprights, and vice versa.

Different aspects of the present invention provide a unique system and approach which provides correction more effectively and more comfortably than known solutions. Certain novel and unique feature, alone or in combination, create a tolerable and more comfortable brace.

A portion of the foot that goes through excursion during weight bearing for a person with Medial Instability is the medial malleolus. Therefore, an effective brace design should offer control of the medial movement of the medial malleolus. However, the medial malleolus is a bonny prominence that normally has very little soft tissue to cushion it from the outside. Therefore the medial malleolus is intolerant of high corrective pressures due to pain. Yet, if controlled, the medial malleolus is a very effective area in the management of Medial Instability.

Therefore as seen for example in FIG. 1, the preferred embodiment offers a brace having a malleolar window 10 which is an aperture in the lower medial upright 17 and defined thereby, so as to allow at least a portion of the medial malleolus to protrude through the interior wall of the lower medial upright. Thus corrective forces may be applied to the medial malleolus area in a controlled manner. These forces are applied to the tissue around the malleolus, avoiding the pain associated with the application of force directly thereto.

Figure 7:
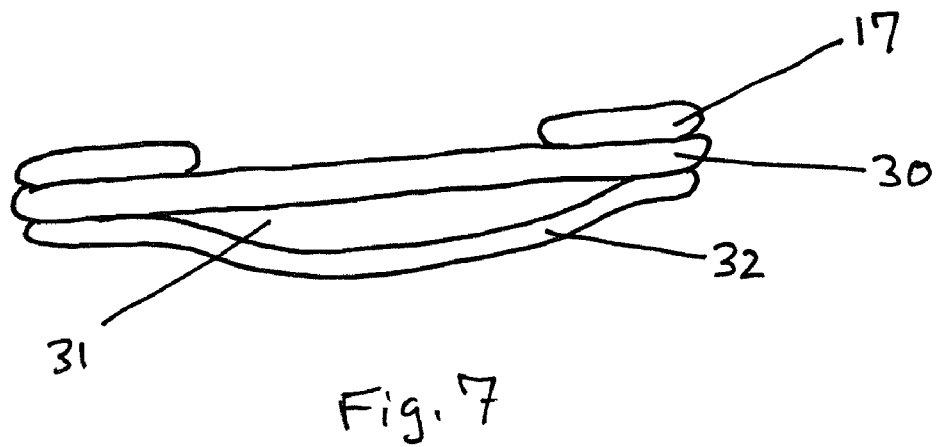
FIG. 7 shows a cutaway of cross-section GG view of a version of an aperture configuration.

In a preferred embodiment, a membrane 12 of flexible material extends over the aperture to provide better support and cushioning, creating a more complete, hammock like support. The membrane preferably comprises an inner and an outer layer, where the inner layer comprises soft cushioning material and the outer layer comprises material that is elastic but having sufficient resiliency and low coefficient of friction to provide good support while conforming to the malleolus shape. Still more preferably is a layer of gel sandwiched between the inner and outer layers. Examples of appropriate material for the membrane are leather, naugahide 32, Pleather™, Neoprene™, Aliplast™, foam 30, gel 31 and textiles. Such material may be obtained for example from Pel Supply company in Cleveland, Ohio under the trade name Volara™. It should be noted that the construction provided in FIG. 7 is in accordance with the most preferred embodiment, but that the membrane may be constructed from a any appropriate material and that single layer or multiple layers of similar or dissimilar materials may be used, and the invention extends to such membrane embodiments.

The medial and lateral malleolli define roughly the hinging axis of the foot. The obvious location for a brace hinging axis is therefore at the vicinity of this axis, and previous solutions have used primarily this axis as the hinge point. In the present invention an aperture exists at that axis, and placing the axis at the window will require complex and bulky setup. The hinge on the windowed side of the brace may be placed above the maleollar window 10, and preferably posterior to the malleolus. Therefore, in the preferred embodiment, one hinge 23 is located adjacent to its respective malleolus, while a second hinge 13 is located above and preferably (in the medial instability case) posterior to, its respective malleolus. While this hinge arrangement causes some relative motion between the upwardly hinged upright and the leg, such movement is minimal and easily tolerated by the patient.

While the relative motion may be largely ignored, it is preferred that the inner surface of the upwardly hinged upright be made of smooth material. This objective may be achieved by using smooth plastic, however the most preferred embodiment utilizes a soft material such as foam padding disposed on the upper upright. In the most preferred embodiment, the inner surfaces of both uprights are covered with such material.

Another optional feature of the most preferred embodiment is termed the medial extension herein. This feature represents a significant and non-obvious advantage over prior brace designs which use a lateral wall extending most of the length of the fifth metatarsal bone to help control the forefoot from abducting. This lateral wall approach is very uncomfortable and many find it intolerable. The medial extension 60 of the present invention utilizes the shoe for forefoot abduction control. Without the medial extension or lateral wall, the forefoot would be free to abduct and push the shoe laterally. The medial wall holds the shoe in place. When the forefoot attempts to abduct with a well fitting shoe, it cannot easily do so. Therefore, during use this preferred embodiment recruits the shoe as a structural lateral support of the system.

Yet another feature provided by the most preferred embodiment is referred to as a fifth ray cut out. An orthosis or brace occupies significant space in a shoe and often users of orthopedic braces face difficulties trying to find shoes of sufficient size to accommodate the brace and foot combination. Common braces have a bottom portion known as the footplate 22, extending longitudinally across at least a part of the length of the foot, and laterally across the bottom of the foot, to provide support. Therefore, the preferred embodiment of the invention provides significant advantages by extending the sole laterally only up to, but not including, the area substantially under the lateral metatarsal, the area commonly know as 'fifth ray' or 'fifth metatarsal' area'. Therefore the footplate has a longitudinal cutout 80 proximal and inferior to the fifth metatarsal when the brace is used. Eliminating the extra bulk under the fifth metatarsal contributes to solving that problem. This is what we termed the Fifth Ray Cut Out (80). Moreover, the result is also better control of the Medial Instability. By eliminating material under the lateral side of the forefoot, the effect is a more medial upward pressure from the material that was not eliminated. Some may refer to this as a medial wedge or medial posting. Every opportunity to provide more support on the medial side of the foot contributes to reduce localized corrective pressure making the brace more tolerable and effective.

Figure 5:
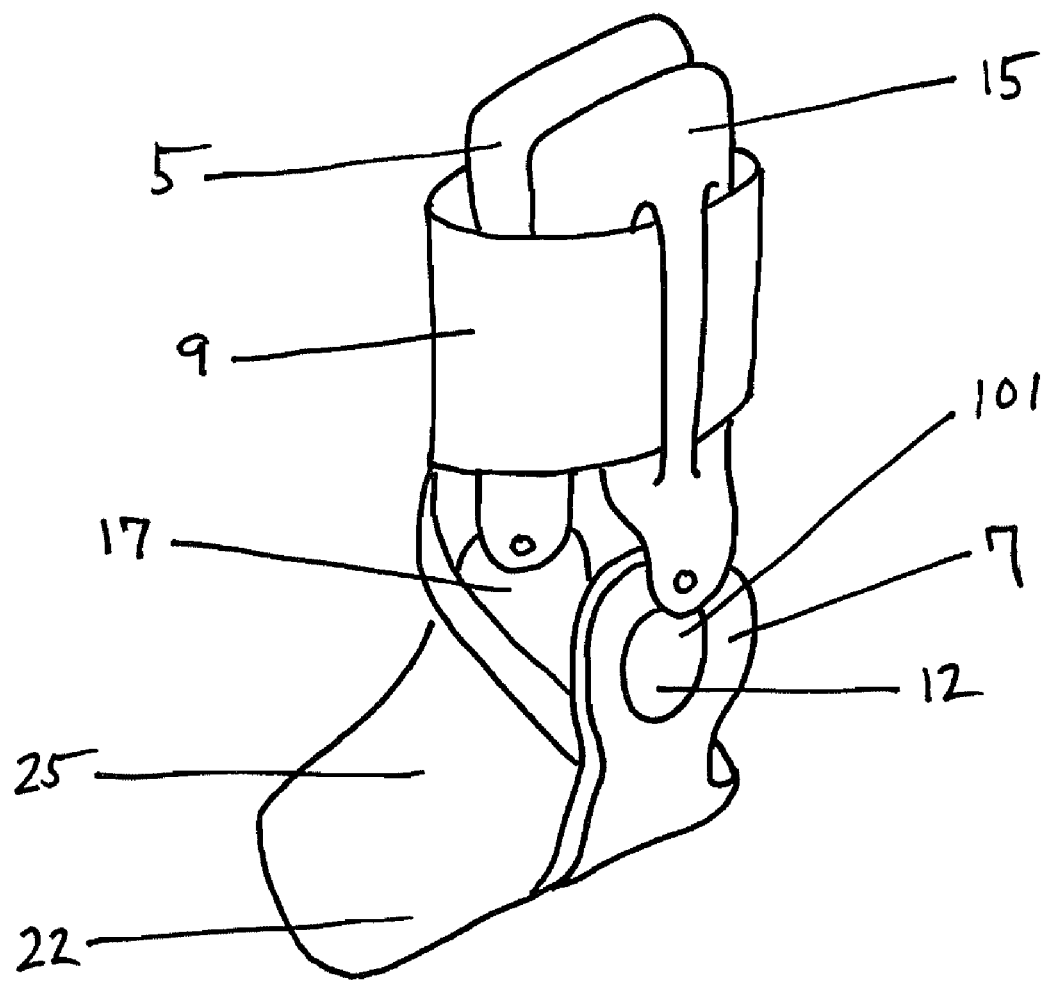
FIG. 5 shows an oblique lateral view of the preferred embodiment as applied to a Lateral Instability condition.
Figure 6:
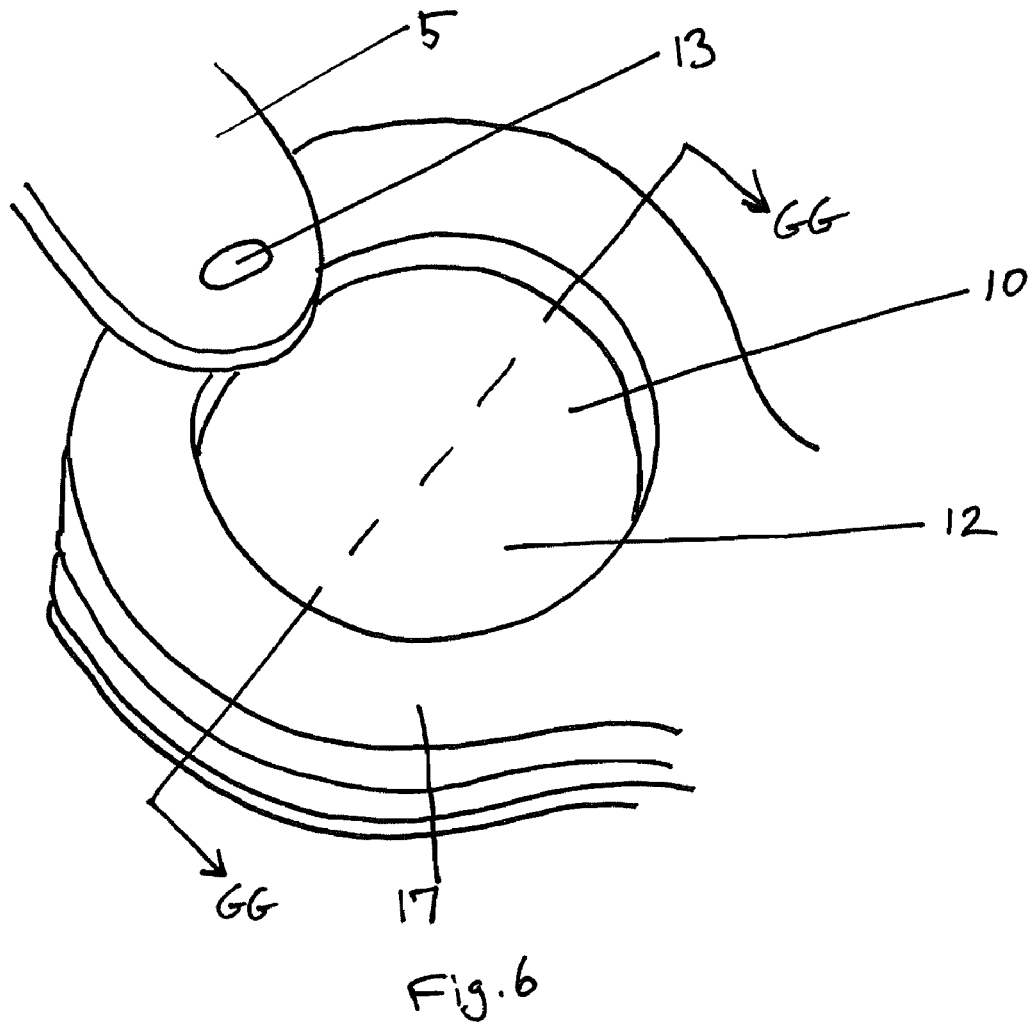
FIG. 6 shows an oblique view of the aperture with a membrane configuration

FIG. 5 depicts a brace designed to treat lateral instability. As can be seen, the lateral lower upright is the upright having the malleolar window 101 for the lateral malleolus, and it is also the upright in which the hinge is located upwardly from the malleolus.

The preferred embodiment further provides a strap 9 for securing the brace to the leg, and a wedge like portion 20 under the footplate that provides an outflare type of support to the sustentaculum tali. In order to mitigate pressure to the sustentaculum tali, padding 4 is provided on the top portion of the footplate 22.

It will be appreciated that the invention is not limited to what has been described hereinabove merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

What is claimed is:

1. A hinged ankle foot brace comprising:
   a heel stirrup;
   a medial and a lateral lower uprights extending substantially vertically from said stirrup, one of said lower uprights defining an aperture dimensioned for receiving at least a portion of a malleolus disposed therein;
   a medial and a lateral upper uprights respectively coupled to said lower uprights, said lateral upper upright hingedly coupled to said lateral lower upright, and said medial upper upright hingedly coupled to said medial lower upright;
   wherein a respective upper upright coupled to said lower upright having the aperture is pivotally hinged upwardly from the center of said aperture; and,
   the opposing upper upright is coupled to said respective lower upright adjacent to the malleolus opposite the malleolus at least partially disposed within said aperture.

2. A hinged ankle foot brace as claimed in claim 1 further comprising a membrane extending over said aperture.

3. A hinged ankle foot brace as claimed in claim 2 wherein said membrane comprises a cushioning inner portion, and a resilient outer portion.

4. A hinged ankle foot brace as claimed in claim 1 wherein said stirrup is constructed as a footplate with a longitudinal cutout adapted to extend proximal and inferior to the fifth metatarsal bone of a patient's foot.

5. A hinged ankle foot brace as claimed in claim 1 wherein:
said upright having said aperture is the medial lower upright;
said medial upper upright is hinged to said lower medial upright upwardly and posteriorly to said aperture; and,
said lateral upper upright is hinged to said lateral lower upright adjacent to the lateral malleolus.

6. A hinged ankle foot brace as claimed in claim 5 further comprising a membrane extending over said aperture.

7. A hinged ankle foot brace as claimed in claim 5 wherein said membrane comprises a cushioning inner portion, and a resilient outer portion.

8. A hinged ankle foot brace as claimed in claim 5 wherein said membrane comprises a cushioning inner portion, and a resilient outer portion.

9. A hinged ankle foot brace as claimed in claim 1 wherein said upright having said aperture is the lateral lower upright
said lateral upper upright is hinged to said lateral lower upright upwardly to said aperture; and,
said medial upper upright is hinged to said medial lower upright adjacent to the medial malleolus.

10. A hinged ankle foot brace as claimed in claim 1, wherein said respective upper upright coupled to said lower upright having the aperture is hinged upwardly and laterally offset from the center of said aperture.

* * * * *